(12) United States Patent
White et al.

(10) Patent No.: US 11,643,215 B2
(45) Date of Patent: May 9, 2023

(54) USE OF CARBON DIOXIDE SENSORS FOR AIRCRAFT VENTILATION CONTROL

(71) Applicant: Honeywell International Inc., Morris Plains, NJ (US)

(72) Inventors: Christopher James White, Yeovil (GB); Jan Ludvik, Jesenice (CZ)

(73) Assignee: Honeywell International Inc., Charlotte, NC (US)

( * ) Notice: Subject to any disclaimer, the term of this patent is extended or adjusted under 35 U.S.C. 154(b) by 199 days.

(21) Appl. No.: 16/897,076

(22) Filed: Jun. 9, 2020

(65) Prior Publication Data
US 2021/0380259 A1    Dec. 9, 2021

(51) Int. Cl.
*B64D 13/06* (2006.01)
*B64D 13/04* (2006.01)
(Continued)

(52) U.S. Cl.
CPC ............. *B64D 13/06* (2013.01); *B64D 13/04* (2013.01); *B64D 13/08* (2013.01); *G01F 9/001* (2013.01);
(Continued)

(58) Field of Classification Search
CPC ........ B64D 13/06; B64D 13/04; B64D 13/08; B64D 2013/0603; B64D 2013/0618;
(Continued)

(56) References Cited

U.S. PATENT DOCUMENTS 4,742,761 A * 5/1988 Horstman .............. B64D 13/04
454/238
5,695,396 A   12/1997 Markwart et al.
(Continued)

FOREIGN PATENT DOCUMENTS

EP    2671801 A2   12/2013
EP    2789537 A1   10/2014
(Continued)

OTHER PUBLICATIONS

Extended Search Report from counterpart European Application No. 21174853.8 dated Nov. 8, 2021, 8 pp.
(Continued)

*Primary Examiner* — Eric S Ruppert
*Assistant Examiner* — Kirstin U Oswald
(74) *Attorney, Agent, or Firm* — Shumaker & Sieffert, P.A.

(57) ABSTRACT

A system includes a concentration sensor, a flow sensor, and a controller. The concentration sensor is configured to measure a concentration of a contaminant in a cabin of an aircraft. The flow sensor is configured to measure a flow rate of air into the cabin. The controller is configured to determine whether a concentration measurement of the contaminant in the cabin exceeds a first concentration threshold. The controller is configured to, in response to determining that the concentration measurement does not exceed the first concentration threshold, control the flow rate of air into the cabin based on a flow rate setpoint. The controller is configured to, in response to determining that the concentration measurement exceeds the first concentration threshold, control the flow rate of air into the cabin based on a flow rate setpoint and a correction factor that is based on a flow sensor tolerance.

20 Claims, 5 Drawing Sheets

(51) Int. Cl.
  *B64D 13/08* (2006.01)
  *G01N 33/00* (2006.01)
  *G01F 9/00* (2006.01)

(52) U.S. Cl.
  CPC ... *G01N 33/004* (2013.01); *B64D 2013/0603* (2013.01)

(58) Field of Classification Search
  CPC ........ G01F 9/001; G01N 33/004; F24F 11/64; F24F 11/74; F24F 2110/50; F24F 2110/70; Y02B 30/70; Y02T 50/50
  USPC .......................................................... 62/89
  See application file for complete search history.

(56) References Cited

U.S. PATENT DOCUMENTS

| | | | |
|---|---|---|---|
| 5,791,982 A * | 8/1998 | Curry .................... | B64D 13/06 454/76 |
| 6,551,184 B1 * | 4/2003 | Mayer .................... | B64D 13/08 454/120 |
| 7,837,541 B2 | 11/2010 | Gray et al. | |
| 9,089,721 B1 * | 7/2015 | Horstman ................ | A62B 7/14 |
| 9,776,725 B2 | 10/2017 | Fox et al. | |
| 9,880,139 B2 | 1/2018 | Moenkemoeller | |
| 9,957,052 B2 | 5/2018 | Fox et al. | |
| 2008/0283663 A1 * | 11/2008 | Space ................... | B64D 13/06 244/118.5 |
| 2009/0139210 A1 * | 6/2009 | Sanchez ............. | G01N 27/4175 60/276 |
| 2016/0214723 A1 * | 7/2016 | Fox ........................ | B64D 13/06 |
| 2017/0003258 A1 * | 1/2017 | Krauss ................. | G01N 21/274 |
| 2018/0148182 A1 | 5/2018 | Fagundes et al. | |
| 2018/0224145 A1 * | 8/2018 | Tajima ................... | B01D 53/18 |
| 2019/0100318 A1 * | 4/2019 | Space ................... | B01D 53/72 |
| 2019/0338965 A1 * | 11/2019 | O'Brian ................ | F24F 11/77 |

FOREIGN PATENT DOCUMENTS

| | | |
|---|---|---|
| EP | 3050801 A1 | 8/2016 |
| EP | 3587267 A1 | 1/2020 |

OTHER PUBLICATIONS

Response to Extended Search Report dated Nov. 8, 2021, from counterpart European Application No. 21174853.8, filed Dec. 13, 2021, 33 pp.

Jung, H., "Modeling CO2 Concentrations in Vehicle Cabin," SAE Technical Paper 2013-01-1497, SAE 2013 World Congress & Exhibition, SAE International; Apr. 2013, 6 pp.

Kos et al., "On-board air quality—Final Report on the effect of new materials," Project: Mitigating risks of fire, smoke and fumes, Grant Agreement No. 640597, Version 2.0, Future Sky Safety, May 2018, 67 pp.

Communication pursuant to Article 94(3) EPC from counterpart European Application No. 21174853.8 dated Jan. 2, 2023, 4 pp.

* cited by examiner

USE OF CARBON DIOXIDE SENSORS FOR AIRCRAFT VENTILATION CONTROL

STATEMENT REGARDING FEDERALLY SPONSORED RESEARCH OR DEVELOPMENT

This invention was made with Government support under Contract No.: 113109 awarded by (UK ATI)—United Kingdom—Aerospace Technologies Institute/UKRI (Innovate UK). The Government has certain rights in the invention.

TECHNICAL FIELD

The present disclosure relates to systems and techniques for controlling aircraft ventilation.

BACKGROUND

An environmental control system provides clean, pressurized air to a cabin of an aircraft. This pressurized air may be supplied from a variety of sources, such as bleed air from an engine, a cabin air compressor (CAC), or an auxiliary power unit (APU). To produce an adequate supply of pressurized air to the cabin, these pressurized air sources consume fuel or energy.

SUMMARY

Aircraft ventilation systems described herein may reduce an amount of fuel or energy consumed by pressurized air sources by more accurately controlling a flow of clean, pressurized air to the cabin.

In some examples, the disclosure describes a system for controlling flow of clean, pressurized air to a cabin of an aircraft. The system includes a concentration sensor, a flow sensor, and a controller. The concentration sensor is configured to measure a concentration of a contaminant in the cabin of the aircraft. The flow sensor is configured to measure a flow rate of air into or out of the cabin. The controller is configured to determine whether a concentration measurement of the contaminant in the cabin exceeds a first concentration threshold. In response to determining that the concentration measurement does not exceed the first concentration threshold, the controller is configured to control the flow rate of air into the cabin based on a flow rate setpoint. In response to determining that the concentration measurement exceeds the first concentration threshold, the controller is configured to control the flow rate of air into the cabin based on a flow rate setpoint and a correction factor, wherein the correction factor is based on a flow sensor tolerance.

In some examples, the disclosure describes a system for controlling flow of clean, pressurized air to a cabin of an aircraft. The system includes a concentration sensor, a flow sensor, and a controller. The concentration sensor is configured to measure a concentration of a contaminant in the cabin. The flow sensor is configured to measure a flow rate of pressurized air to the cabin from an environmental control system. The controller is implemented in circuitry and in communication with the concentration sensor and the flow sensor. The controller is configured to control the flow rate of pressurized air into the cabin to maintain a concentration measurement of the contaminant in the cabin at or below a first concentration threshold. The controller is also configured to control the flow rate of pressurized air into the cabin to maintain the flow rate of pressurized air into the cabin above a flow rate setpoint. The flow rate setpoint does not account for a tolerance of the flow sensor at the flow rate.

In some examples, the disclosure describes a method for controlling flow of clean, pressurized air into a cabin of an aircraft. The method includes measuring, by a concentration sensor, a concentration of a contaminant in the cabin and measuring, by a flow sensor, a flow rate of air into or out of the cabin. The method includes determining, by a controller, whether the concentration measurement of the contaminant in the cabin exceeds a first concentration threshold. In response to determining that the concentration measurement does not exceed the first concentration threshold, the method includes controlling the flow rate of air into the cabin based on a flow rate setpoint. In response to determining that the concentration measurement exceeds the first concentration threshold, the method includes controlling the flow rate of air into the cabin based on a flow rate setpoint and a correction factor, in which the correction factor is based on a flow sensor tolerance.

The details of one or more examples are set forth in the accompanying drawings and the description below. Other features, objects, and advantages will be apparent from the description and drawings, and from the claims.

BRIEF DESCRIPTION OF THE FIGURES

The details of one or more examples are set forth in the accompanying drawings and the description below. Other features, objects, and advantages will be apparent from the description and drawings, and from the claims.

DETAILED DESCRIPTION

In general, an environmental control system (ECS) of an aircraft may supply clean, pressurized air to a cabin of the aircraft based on minimum flow rate limits established by regulatory agencies, such as the Federal Aviation Administration (FAA). These minimum flow rate limits typically take into account a number of occupants in the cabin and are determined using relatively conservative estimates related to the oxygen consumed and waste produced by an occupant. For example, a typical minimum flow rate limit may be about 0.55 pounds of air per minute per occupant of a cabin. A control system of the ECS may measure a flow rate of clean, pressurized air using a flow meter and control the flow rate above the minimum flow rate limit. However, flow meters typically have relatively low accuracy at low flow rates. To compensate for this low accuracy and ensure operation above the minimum flow rate limits, the control system may control the flow rate of the clean, pressurized air based on a tolerance of the flow meters that corresponds to the lower accuracy, such that the actual flow rate of the clean, pressurized air into the cabin is higher than the minimum flow rate limit. As a result of this added tolerance, the control system may cause the aircraft to pressurize and cool a greater amount of air, and thereby consume a greater amount of fuel and/or energy, than would otherwise be required to meet the minimum flow rate limits.

According to various examples described herein, a control system of an ECS may be configured to control a flow of clean, pressurized air above mandated minimum flow rate limits with a reduced or eliminated tolerance by supplementing flow rate measurements of a flow meter with contaminant measurements of a contaminant sensor. In contrast to a flow meter, which may have reduced accuracy at low flow rates, contaminant sensors, such as carbon dioxide sensors, may have relatively high accuracy compared to flow meters. As described above, the minimum flow rate limits may be based on assumptions regarding a numbers occupants of the cabin, and a corresponding amount of clean, pressurized air for personal comfort and safety. These assumptions may be extended to one or more contaminant limits, such as a maximum carbon dioxide concentration and/or a humidity range, that correspond to a minimum flow rate limit. As long as the contaminant concentration remains above the one or more contaminant limits, the control system may use flow rate measurement of the flow meter to control the flow rate of the clean, pressurized air above the minimum flow rate limit, but below the tolerance of the flow meter. In this way, the control system may reduce an amount of clean, pressurized air above the minimum flow rate limits that is supplied to the cabin, thereby reducing an amount of fuel or energy consumed by the ECS.

Figure 1:
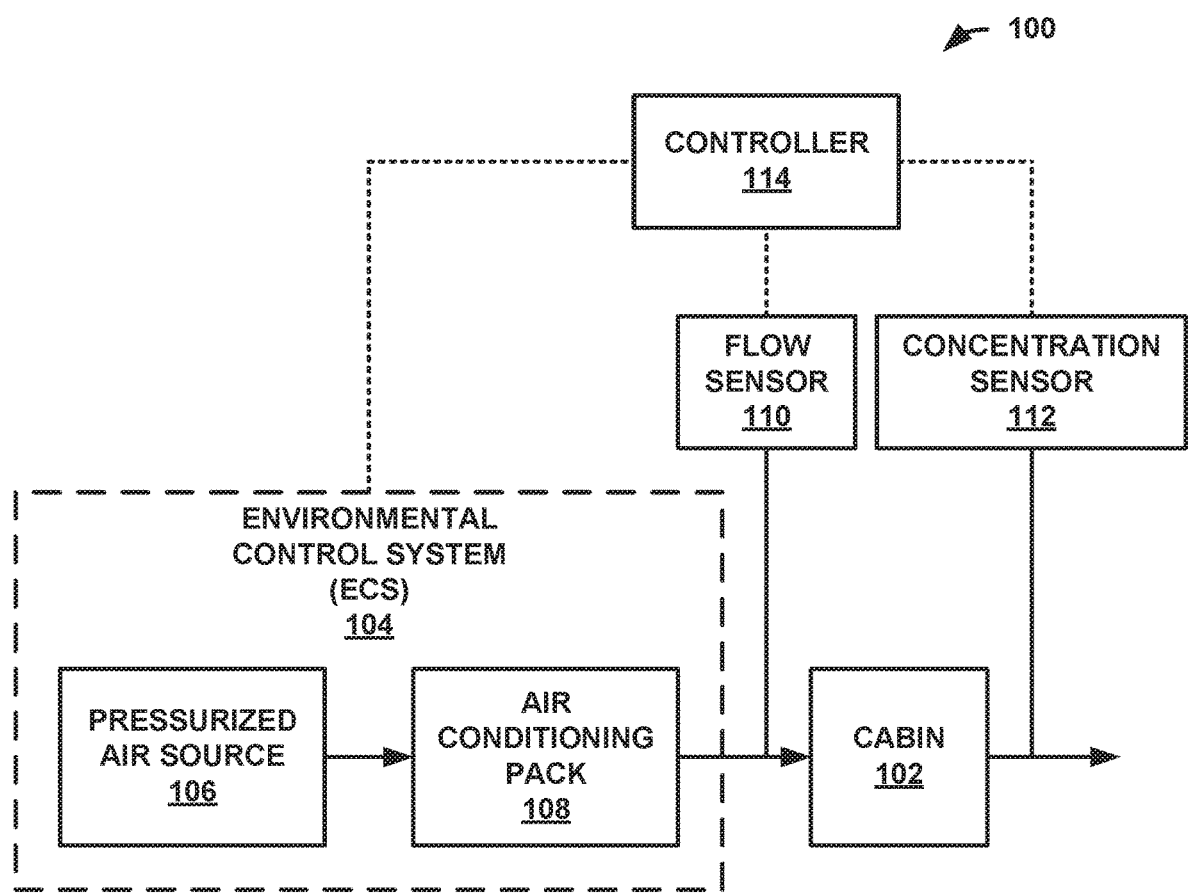
FIG. 1 is a diagram illustrating an example system for supplying clean, pressurized air to a cabin of an aircraft.

FIG. 1 is a diagram illustrating an example system 100 for supplying clean, pressurized air to a cabin 102 of an aircraft. Cabin 102 includes an internal environment that houses occupants. During flight, these occupants produce one or more contaminants, such as carbon dioxide and water vapor.

System 100 includes ECS 104. ECS 104 is configured to supply clean, pressurized air to cabin 102. ECS 104 includes at least one pressurized air source 106. Pressurized air source 106 is configured to generate pressurized air for use in cabin 102. For example, when the aircraft is on the ground, air pressure outside the aircraft may be similar to or the same as air pressure within cabin 102. However, once the air is at higher elevations, the air pressure outside the aircraft may be significantly lower than an air pressure required for cabin 102, such that pressurized air source 106 may supply cabin 102 with pressurized air. Pressurized air source 106 may include a variety of air sources including, but not limited to, a bleed air source (e.g., one of more compression stages of a gas turbine engine), a load compressor (e.g., driven directly by an auxiliary power unit), a stand-alone pressurized air source as cabin air compressors (e.g., driven by electricity from an auxiliary power unit), or any other air source capable of supplying air with a sufficiently high pressure so as to pressurize cabin 102. ECS 104 includes at least one air conditioning pack 108. In the process of compressing the air, pressurized air source 106 may heat the air to a relatively high temperature that is not suitable for direct discharge into cabin 102. Air conditioning pack 108 is configured to receive pressurized air from pressurized air source 106 and cool the pressurized air.

System 100 includes at least one flow sensor 110. Flow sensor 110 is configured to measure a flow rate of air into or out of cabin 102. While flow rate will be described herein as mass flow rate (pounds per minute) or mass flow rate per occupant (pounds per minute per occupant) of cabin 102, it will be understood that other flow rate units and representations of measurement (e.g., volumetric) may be used. A variety of flow sensors may be used including, but not limited to, differential pressure flow sensors (e.g., venturi), positive displacement flow sensors (e.g., rotary vane), velocity flow sensors (e.g., sonic), mass flow sensors (e.g., Coriolis), open channel flow sensors (e.g., flumes), or any other flow sensor capable of measuring flow of air from ECS 104 into cabin 102.

System 100 includes at least one concentration sensor 112. Concentration sensor 112 is configured to measure a concentration of a contaminant in cabin 102. While illustrated as measuring a concentration of air discharged from cabin 102, concentration sensor 112 may be configured and/or positioned at any location sufficient to provide an accurate representation of the concentration of the contaminant in cabin 102. In some examples, concentration sensor 112 is a carbon dioxide concentration sensor. For example, in an internal environment that includes primarily human occupants producing bio effluents, carbon dioxide may act as a relatively good proxy air quality in cabin 102. A variety of carbon dioxide sensors may be used including, but not limited to, infrared gas sensors, chemical gas sensors, and the like. In some examples, other gas concentration sensors, such as volatile organic compound (VOC) sensors or hydrocarbon gas sensors may be used to estimate carbon dioxide concentration, such as by generating a carbon dioxide equivalent measurement.

System 100 includes controller 114. Controller 114 is communicatively coupled to flow sensor 110, concentration sensor 112, and ECS 104, and configured to receive measurements from flow sensor 110 and concentration sensor 112 and send control signals to one or more systems of ECS 104, such as pressurized air source 106 and/or air conditioning pack 108. Controller 114 may include any of a wide range of devices, including processors (e.g., one or more microprocessors, one or more application specific integrated circuits (ASICs), one or more field programmable gate arrays (FPGAs), or the like), servers, desktop computers, notebook (i.e., laptop) computers, tablet computers, and the like.

Controller 114 is configured to control ECS 104 to maintain adequate conditions within the internal environment of cabin 102, such as for personal comfort or required by law or industry standard. For example, controller 114 may be configured to control a pressure, temperature, humidity, air flow rate, or other ambient conditions of cabin 102 at various aircraft conditions, such as ground operation, passenger loading, take-off, cruising, descent, and landing. In particular, regulatory agencies, such as the International Civil Aviation Organization (ICAO), FAA, European Aviation Safety Agency (EASA), or Civil Aviation Authority (CAA), may establish minimum flow rate limits regarding air supplied to a cabin of an aircraft. As such, controller 114 is configured to control ECS 104 to supply clean, pressurized air to cabin 102 based on the minimum flow rate limits established by the regulatory agencies. These minimum flow rate limits typically take into account a number of occupants in cabin 102, such as determined by a pilot or other individual responsible for establishing the minimum flow rate limit. The regulatory agencies may determine these minimum flow rate limits using estimates related to contaminants produced by an occupant. Due to variability in an amount of contaminant produced by an individual, these estimates may be relatively conservative.

To comply with the minimum flow rate limits, controller 114 may be configured to measure a flow rate of clean, pressurized air using flow sensor 110. However, flow sensor 110 may be relatively inaccurate at low flow rates. As a result, a tolerance of flow sensor 110 may greater than 5%, such as up to 15%. In contrast, concentration sensor 112 may have a relatively high accuracy, such as a tolerance of about 100 parts per million (ppm). In some instances, such as at low flow conditions experienced during flight (e.g., for a large commercial aircraft, a flow rate of less than about 100 pounds per minute and a carbon dioxide concentration less than about 2000 ppm), a tolerance of concentration sensor 112 may be lower than a tolerance of flow sensor 110. In some instances, such as at lower-than-expected contaminant generation levels, a contaminant concentration may be substantially lower than a safety limit, even if a tolerance of concentration sensor 112 is higher than a tolerance of flow sensor 110.

Controller 114 is configured to control a flow of clean, pressurized air above mandated minimum flow rate limits with a reduced or eliminated tolerance by supplementing flow rate measurements of flow sensor 110 with contaminant concentration measurements of concentration sensor 112. As described above, the minimum flow rate limits may be based on assumptions regarding a numbers occupants of the cabin, and a corresponding amount of clean, pressurized air for personal comfort and safety. These assumptions may be extended to one or more contaminant concentration limits, such as a maximum carbon dioxide concentration and/or a humidity range, that correspond to the minimum flow rate limit as measured by flow sensor 110. As long as the contaminant concentration remains below the one or more contaminant limits corresponding to the actual minimum flow rate limits (e.g., without flow sensor tolerance), the control system may use flow rate measurement of the flow meter to control the flow rate of the clean, pressurized air at or above the minimum flow rate limit, but below the tolerance of the flow meter. In this way, system 100 may reduce an amount of clean, pressurized air above the minimum flow rate limits that is supplied to the cabin, thereby reducing an amount of fuel or energy consumed by the ECS.

Controller 114 is configured to receive concentration measurements from concentration sensor 112. As explained above, concentration sensor 112 may have a concentration sensor tolerance that, while lower than a flow sensor tolerance, may be accounted for. As such, controller 114 may determine a concentration measurement that includes a concentration tolerance of concentration sensor 112. Controller 114 is configured to determine whether a concentration measurement of the contaminant in cabin 102 exceeds a concentration threshold. The concentration threshold may correspond to the minimum flow rate limit for the contaminant in cabin 102. Rather than maintain this minimum flow rate limit using only flow rate measurements, which may have relatively high tolerance, controller 114 may be configured to use concentration measurements, which have relatively low tolerance.

In response to determining that the concentration measurement does not exceed the concentration threshold, controller 114 is configured to control the flow rate of air into the cabin based on the minimum flow rate limit without compensating for flow sensor tolerance. In response to determining that the concentration measurement exceeds the concentration threshold, controller 114 is configured to control the flow rate of air into cabin 102 based on the minimum flow rate limit and a correction factor. The correction factor is based on a flow sensor tolerance. For example, the correction factor may be a step-wise correction factor that adds in the entire flow sensor tolerance above the concentration threshold (e.g., the "first concentration threshold" described in FIG. 2), or may be an incremental correction factor that adds in partial flow sensor tolerance that is proportional up to an upper concentration threshold (e.g., the "second concentration threshold" described in FIG. 2).

As described above, controller 114 may be configured to maintain a contaminant concentration below one or more concentration thresholds. In some examples, the concentration threshold may be a pre-determined maximum contaminant concentration limit. For example, the concentration threshold may correspond to a safety and/or comfort limit for occupants of cabin 102. A certification authority may establish and/or approve the predetermined contaminant concentration limits that correspond to one or more minimum flow rate limit. These concentration thresholds may be less arbitrary than an occupant-based minimum flow rate limit.

In some examples, the correction factor and the concentration threshold are based on a model of a contaminant concentration for cabin 102 ("cabin model"), such as based on simulated and/or historical data for cabin 102. For example, a contaminant concentration for cabin 102 (or another cabin, such as a same type or having similar characteristics as cabin 102) and a flow rate of air to cabin 102 may be measured and tracked over time, such as during operation or testing, to determine a safe contaminant limit and/or identify factors that may influence contaminant concentrations. Such measurement and tracking may include other factors that may influence contaminant production, such as a number of occupants, a duration of flight, a time of day, an altitude of flight, and the like. The measured and tracked contaminant concentrations and flow rates may be used to build the cabin model representing contaminant concentration as a function of number of occupants (among other factors) and flow rate of air into cabin 102. As another example, a contaminant concentration for cabin 102 and a flow rate of air to cabin 102 may be simulated, such as based on various equations and/or in combination with historical data described above, to build the cabin model. In some instances, the cabin model may be developed and/or approved by a certification authority. For example, the certification authority may evaluate the tracked and/or simulated contaminant concentrations and flow rates for accuracy and/or suitability. By using these cabin models, controller 114 may be configured to enforce the minimum flow rate limit as a concentration measurement using concentration sensor 112, rather than a flow rate measurement using flow sensor 110.

In this way, system 100 may reduce an amount of power used to supply pressurized air to cabin 102. For example, to pressurize and cool the air for use in cabin 102, ECS 104 may consume significant amounts of power. As such, any increase in an amount of pressurized air may cost substantial fuel that may otherwise be used for propulsion or electrical power production. By reducing an amount of pressurized air, system 100 may reduce the amount of power while also maintaining existing limits on a minimum flow rate limit.

Figure 2:
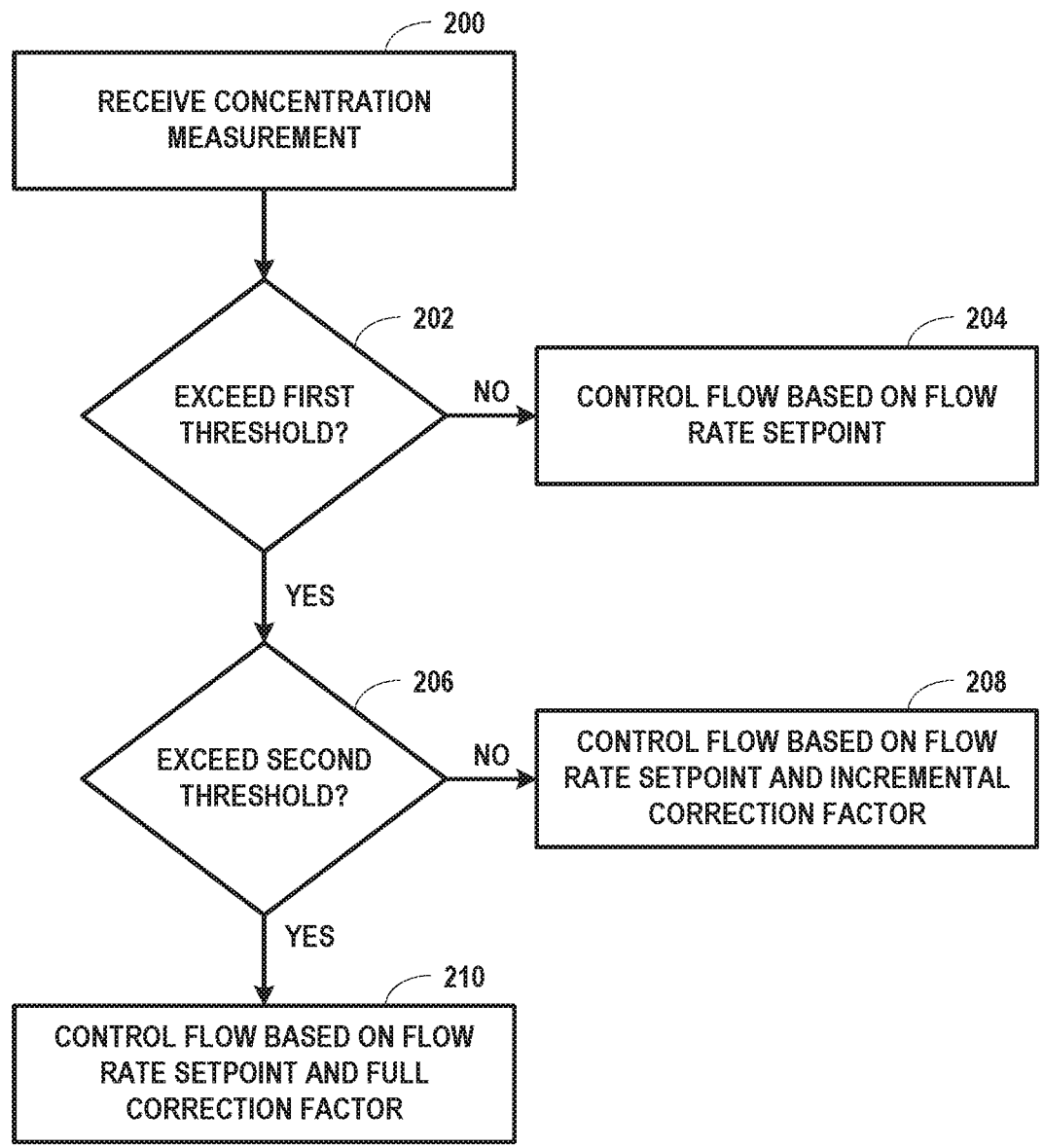
FIG. 2 is a flowchart of an example technique for supplying clean, pressurized air to a cabin of an aircraft.

FIG. 2 is a flowchart of an example technique for supplying clean, pressurized air to a cabin of an aircraft. The example technique of FIG. 2 will be described with respect to system 100 of FIG. 1; however, other systems may be controlled with the example technique of FIG. 2.

Controller 114 receives a concentration measurement of a contaminant in cabin 102 (200). For example, concentration sensor 112 may measure the concentration of the contaminant, such as carbon dioxide, in cabin 102 and send the concentration measurement to controller 114. Controller 114 may also receive a flow rate measurement of a flow rate of pressurized air into or out of cabin 102. For example, flow sensor 110 may measure the flow rate of air into cabin 102 and send the flow rate measurement to controller 114.

Controller 114 may determine whether the concentration measurement of the contaminant in the cabin exceeds a first concentration threshold (202). The first concentration threshold may represent a concentration corresponding to a flow rate setpoint. Controller 114 may determine the flow rate setpoint based on the minimum flow rate limit and a number of occupants of cabin 102. Controller 114 may determine the first concentration threshold based on the flow rate setpoint and a cabin model. The cabin model may represent a predicted contaminant concentration based on the number of occupants. In some examples, the cabin model may be established with a regulatory agency. For example, the regulatory agency may set the cabin model such that the flow rate setpoint represents a safe contaminant concentration. In some examples, the cabin model may be established using simulated and/or historical data. For example, data related to contaminant concentration may be collected over a period of time and used to build a model that correlates a particular flow rate setpoint with a particular contaminant concentration.

In response to determining that the concentration measurement does not exceed the first concentration threshold, controller 114 may control the flow rate of air into cabin 102 based on the flow rate setpoint (204). The flow rate setpoint may be the flow rate setpoint that does not include a tolerance of flow sensor 110. For example, based on the cabin model, the concentration measurement may correspond to an actual flow rate that is greater than or equal to the flow setpoint without any discount for flow sensor tolerance. As such, rather than accounting for flow sensor tolerance, which may lead to overproduction of air, controller 114 may control the flow rate at the measured flow rate.

In response to determining that the concentration measurement exceeds the first concentration threshold, controller 114 may control the flow rate of air into cabin 102 based on the flow rate setpoint and a correction factor. The correction factor is based on a flow sensor tolerance. For example, based on the cabin model, the concentration measurement may correspond to an actual flow rate that is less than the flow rate setpoint. This may be due to a deviation of actual behavior from the cabin model (e.g., higher than expected respiration) or a relatively low accuracy of flow sensor 110 and/or concentration sensor 112.

In the example of FIG. 2, in response to determining that the concentration measurement exceeds the first concentration threshold, controller 114 may determine whether the concentration measurement of the contaminant exceeds a second threshold (206). In response to determining that the concentration measurement exceeds the first concentration threshold, controller 114 may control the flow rate of air into cabin 102 based on the flow rate setpoint and an increment of the correction factor (208). For example, a concentration between the first and second concentration thresholds may correspond to a minimum flow rate limit that includes a partial flow sensor tolerance. This incremental correction factor may still represent a reduction in actual flow rate compared to a full flow sensor tolerance, as the concentration sensor tolerance is less than the flow sensor tolerance.

In response to determining that the concentration measurement exceeds the second concentration threshold, controller 114 may control the flow rate of air into cabin 102 based on the flow rate setpoint and a full correction factor (210). For example, the second concentration threshold may correspond to a minimum flow rate limit that includes a full flow sensor tolerance.

Figure 3A:
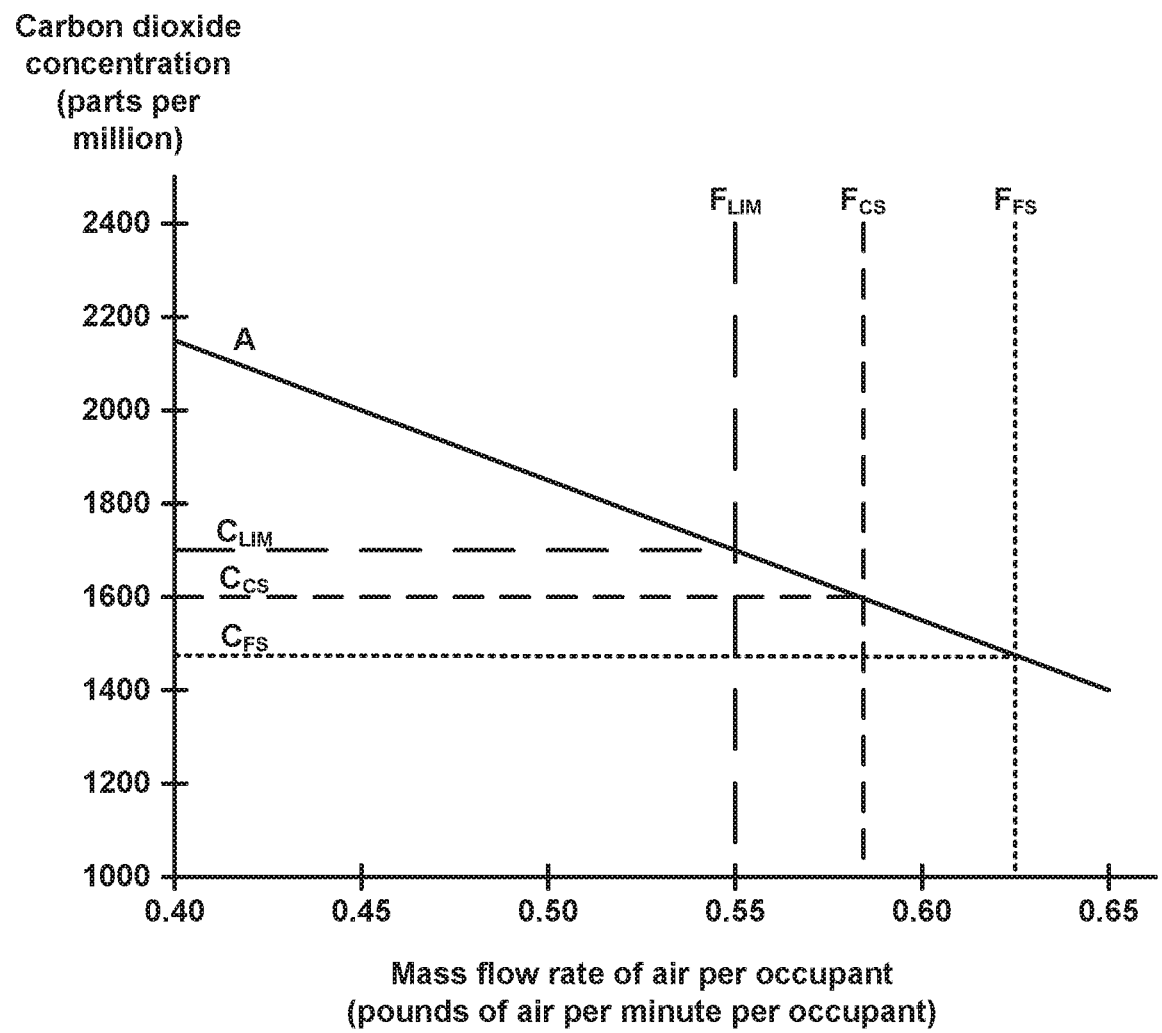
FIG. 3A is an example graph of a carbon dioxide limits corresponding to minimum flow rate limits.

FIG. 3A is a theoretical, example graph of carbon dioxide limits corresponding to flow rate limits. Line A represents a predicted model of carbon dioxide concentration in cabin 102 at different flow rates per occupant. While shown as linear model, line A may have other shapes, and may be dependent on other conditions (e.g., a number of occupants in cabin 102). For example, as a number of occupants of cabin 102 increases, and therefore a total flow rate of cabin 102 increases, a tolerance of flow sensor 110 may decrease, such that a flow rate measurement limit ($F_{FS}$) of flow sensor 110 may decrease as a number of occupants increases.

As illustrated in FIG. 3A, a minimum flow rate limit ($F_{LIM}$) corresponds to a carbon dioxide concentration ($C_{LIM}$) of about 1700 ppm. This minimum flow rate limit may represent a maximum allowable carbon dioxide concentration in cabin 102. As described above, controller 114 may control the flow rate of air into cabin 102 to remain below this maximum flow rate limit. Controller 114 may receive concentration measurements from concentration sensor 112 and flow rate measurements from flow sensor 110.

For behavior of carbon dioxide concentration in cabin 102 matching line A, the minimum flow rate limit may correspond to a carbon dioxide concentration measurement from concentration sensor 112 of about 1600 ppm (e.g., a 100 ppm tolerance) and a flow rate measurement from flow sensor 110 of about 0.625 pounds per minute (e.g., a 13% tolerance). If controller 114 operates ECS 104 based only on flow rate measurements ($F_{FS}$) from flow sensor 110 and its corresponding tolerance, controller 114 would operate ECS 104 at a concentration ($C_{FS}$) of about 1475 ppm. However, if controller 114 operates ECS 104 based on carbon dioxide concentration measurements ($C_{CS}$) from concentration sensor 112 and its corresponding tolerance, controller 114 would operate ECS 104 at a flow rate ($F_{CS}$) of about 0.585 pounds per minute, rather than 0.625 pounds per minute.

Figure 3B:
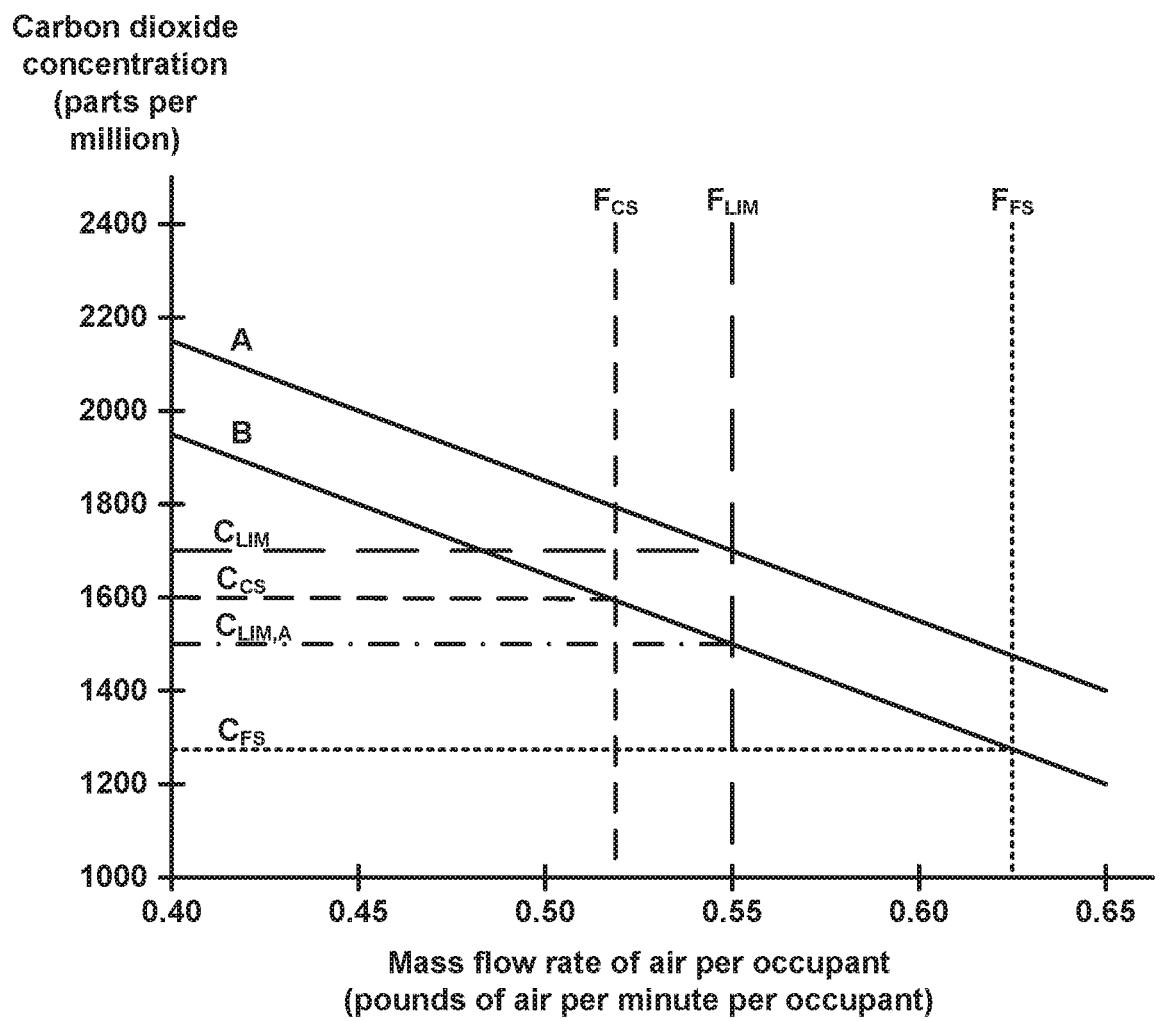
FIG. 3B is an example graph of a carbon dioxide limits corresponding to minimum flow rate limits at potential oversupply.

In some instances, an actual carbon dioxide behavior may deviate from a theoretical or predicted carbon dioxide behavior, such that less air may be required. For example, various operating conditions within a particular aircraft or occupant composition for a particular flight may deviate from the predicted carbon dioxide behavior, such that operation according to the predicted carbon dioxide behavior may cause oversupply of air to cabin 102. FIG. 3B is a theoretical, example graph of carbon dioxide limits corresponding to flow rate per occupant limits at potential oversupply. Line A represents the predicted model of carbon dioxide concentration from FIG. 3A, while Line B represents an actual behavior of carbon dioxide concentration for cabin 102. As explained above, the predicted model for minimum flow rate limits may be based off relatively conservative limits, such that actual carbon dioxide behavior may be lower for a given flight. Rather than operate ECS 104 at the predicted carbon dioxide behavior of Line A, thus oversupplying cabin 102, controller 114 may further reduce the flow rate of air to cabin 102 to better match the actual carbon dioxide behavior shown of Line B.

In the example of FIG. 3B, for behavior of carbon dioxide concentration in cabin 102 matching line B, a carbon dioxide concentration measurement from concentration sensor 112 may remain less than or equal to 1600 ppm for a flow rate ($F_{CS}$) of at or above about 0.515 pounds per minute. If controller 114 operates ECS 104 based only on flow rate measurements ($F_{FS}$) from flow sensor 110 and its corresponding tolerance, controller 114 would operate ECS 104 at a concentration ($C_{FS}$) of about 1275 ppm. However, if controller 114 operates ECS 104 based on carbon dioxide concentration measurements ($C_{CS}$) from concentration sensor 112 and its corresponding tolerance, controller 114 would operate ECS 104 at a flow rate ($F_{CS}$) lower than 0.625 pounds per minute based on the flow rate measurements.

In some examples, the minimum flow rate limit ($F_{LIM}$) may be an absolute minimum flow rate limit. For example, while carbon dioxide concentration measurements may enable controller 114 to reduce or eliminate flow sensor tolerance of flow sensor measurements from flow sensor 110, such flow sensor measurements may not decrease below the minimum flow rate limit. In this example of FIG. 3B, this absolute minimum flow rate limit corresponds to a carbon dioxide concentration ($C_{LIM,A}$) of about 1500 ppm. As such, controller 114 may control the flow rate of air based on the minimum flow rate limit as a flow rate setpoint, and increment the flow rate setpoint based on a correction factor if carbon dioxide concentration exceeds 1600 ppm measurement. However, even with such an absolute flow rate limit, controller 114 may control the flow rate of air to cabin 102 with a reduced flow rate. For example, controller 114 may control the flow rate of air without compensating for either flow sensor tolerance of flow sensor 110 or concentration sensor tolerance of concentration sensor 112.

In some examples, the minimum flow rate limit ($F_{LIM}$) may not be an absolute minimum flow rate limit. For example, the minimum flow rate limit may correspond to a maximum carbon dioxide concentration limit such that, so long as the maximum carbon dioxide concentration limit is maintained, controller 114 may control the flow rate of air below the minimum flow rate limit and based on the carbon dioxide concentration measurements ($C_{CS}$). In the example of FIG. 3B, the minimum flow rate limit, and correspondingly the maximum carbon dioxide concentration limit, may correspond to a carbon dioxide concentration measurement from concentration sensor 112 of about 1600 ppm (e.g., a 100 ppm tolerance) with a flow rate of about 0.515 pounds per minute. As a result, controller 114 may further reduce the air flow beyond the minimum flow rate limit, thereby preserving even more fuel and/or power.

Figure 3C:
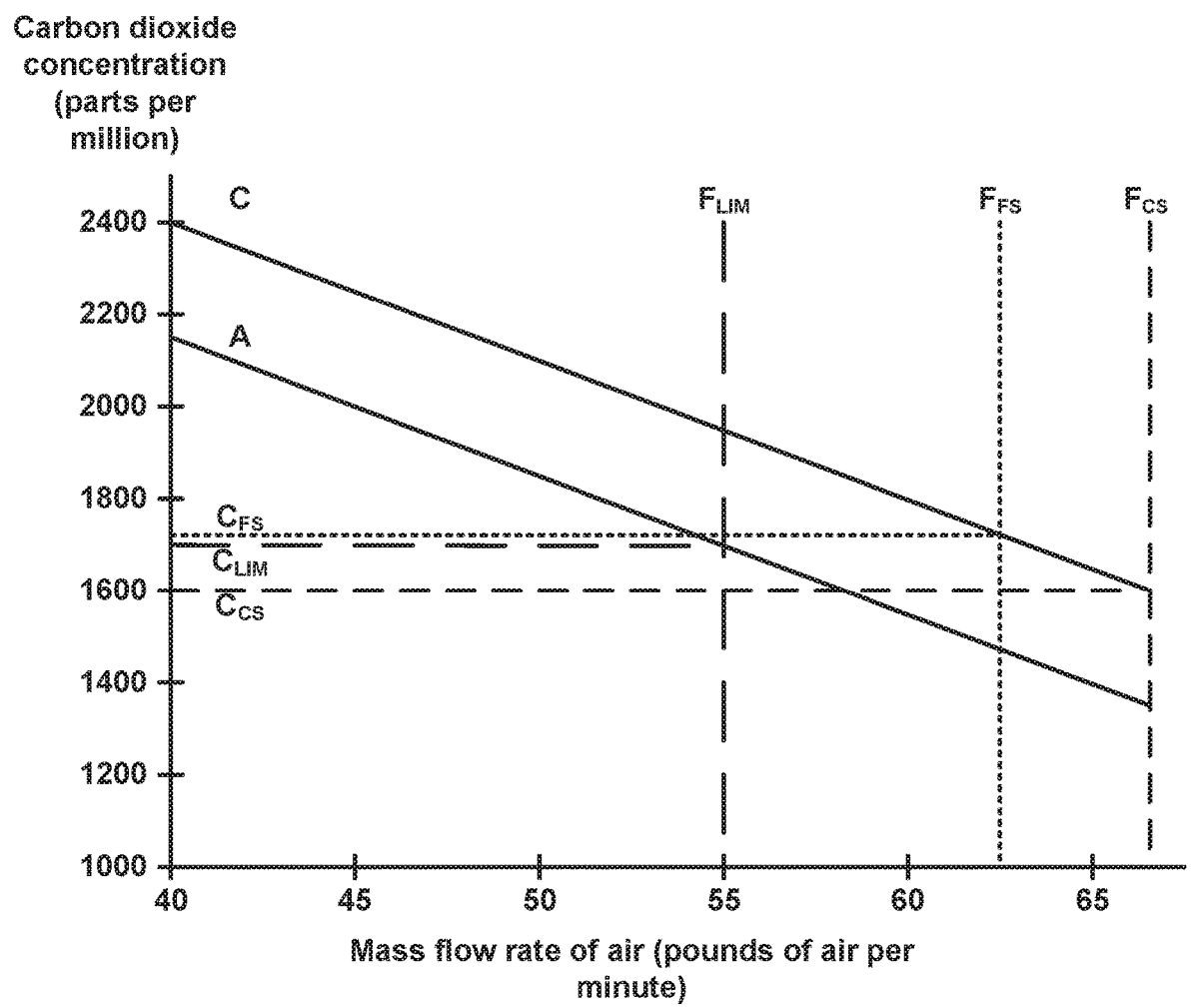
FIG. 3C is an example graph of a carbon dioxide limits corresponding to minimum flow rate limits at potential undersupply.

In some instances, an actual carbon dioxide behavior may deviate from a theoretical or predicted carbon dioxide behavior, such that more air may be required. For example, a human operator may be responsible for selecting a number of occupants in cabin 102. If this number is incorrect (e.g., lower than actual), operation according to the predicted carbon dioxide behavior may cause undersupply of air to cabin 102. FIG. 3C is an example graph of carbon dioxide limits corresponding to flow rate limits at potential undersupply. Line A represents the predicted model of carbon dioxide concentration from FIG. 3A based off an incorrect number of occupants (e.g., 100), while Line C represents an actual behavior of carbon dioxide concentration for cabin 102. In the example of FIG. 3C, the flow rate illustrated in the x-axis is represented according to 100 occupants in cabin 102. However, an actual number of occupants may be higher, such that Line A may not accurately represent behavior of carbon dioxide concentration for cabin 102, such that actual carbon dioxide behavior may be higher. Rather than operate ECS 104 at the predicted carbon dioxide behavior of Line A, thus undersupplying cabin 102, controller 114 may increase the flow rate of air to cabin 102 to better match the actual carbon dioxide behavior shown of Line C.

In the example of FIG. 3C, for behavior of carbon dioxide concentration in cabin 102 matching line C, a carbon dioxide concentration measurement from concentration sensor 112 may remain less than or equal to 1600 ppm for a flow rate ($F_{CS}$) of at or above about 66.5 pounds per minute (corresponding to 0.665 pounds per minute per occupant). If controller 114 operates ECS 104 based only on flow rate measurements ($F_{FS}$) from flow sensor 110 and its corresponding tolerance based on the incorrect occupant count, controller 114 would operate ECS 104 at a concentration ($C_{FS}$) of about 1725 ppm, which is above the maximum carbon dioxide concentration limit ($C_{LIM}$) of 1700 ppm. However, if controller 114 operates ECS 104 based on carbon dioxide concentration measurements ($C_{CS}$) from concentration sensor 112 and its corresponding tolerance, controller 114 would operate ECS 104 at a flow rate ($F_{CS}$) higher than the flow rate measurement of 66 pounds per minute (corresponding to 0.66 pounds per minute per occupant) based on the flow rate measurements, but within the maximum carbon dioxide concentration limit of 1700 ppm (measured as 1600 ppm due to concentration sensor tolerance). In this way, controller 114 may protect cabin 102 from undersupply of air.

The techniques described in this disclosure may be implemented, at least in part, in hardware, software, firmware, or any combination thereof. For example, various aspects of the described techniques may be implemented within one or more processors, including one or more microprocessors, digital signal processors (DSPs), ASICs, FPGAs, or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure.

Such hardware, software, and firmware may be implemented within the same device or within separate devices to support the various techniques described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware, firmware, or software components. Rather, functionality associated with one or more modules or units may be performed by separate hardware, firmware, or software components, or integrated within common or separate hardware, firmware, or software components.

The techniques described in this disclosure may also be embodied or encoded in an article of manufacture including a computer-readable storage medium encoded with instructions. Instructions embedded or encoded in an article of manufacture including a computer-readable storage medium, may cause one or more programmable processors, or other processors, to implement one or more of the techniques described herein, such as when instructions included or encoded in the computer-readable storage medium are executed by the one or more processors. Computer readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or other computer readable media. In some examples, an article of manufacture may include one or more computer-readable storage media.

In some examples, a computer-readable storage medium may include a non-transitory medium. The term "non-transitory" may indicate that the storage medium is not embodied in a carrier wave or a propagated signal. In certain examples, a non-transitory storage medium may store data that can, over time, change (e.g., in RAM or cache).

Examples

Example 1: In one example, a system includes: an environmental control system configured to supply pressurized air to a cabin of an aircraft; a concentration sensor configured to measure a concentration of a contaminant in the cabin of the aircraft; a flow sensor configured to measure a flow rate of the pressurized air into or out of the cabin; and a controller implemented in circuitry and in communication with the concentration sensor and the flow sensor, the controller configured to: determine whether a concentration measurement of the contaminant in the cabin exceeds a first concentration threshold; in response to determining that the concentration measurement does not exceed the first concentration threshold, control the flow rate of air into the cabin based on a flow rate setpoint; and in response to determining that the concentration measurement exceeds the first concentration threshold, control the flow rate of pressurized air into the cabin based on the flow rate setpoint and a correction factor, wherein the correction factor is based on a tolerance of the flow sensor.

Example 2: The system of Example 1, in which the controller is configured to: determine whether the concentration measurement exceeds a second concentration threshold; and in response to determining that the concentration measurement exceeds the first concentration threshold but does not exceed the second concentration threshold, control the flow rate of pressurized air into the cabin based on the flow rate setpoint and an increment of the correction factor.

Example 3: The system of Example 1 or 2, in which the controller is configured to: receive an indication of a number of occupants in the cabin; and determine the flow rate setpoint based on the number of occupants in the cabin and a minimum flow rate limit.

Example 4: The system of any of Examples 1 to 3, wherein the contaminant includes at least one of carbon dioxide or a hydrocarbon.

Example 5: The system of Example 4, in which the concentration sensor is a carbon dioxide sensor, and in which the first threshold is a maximum carbon dioxide concentration limit associated with the flow rate setpoint.

Example 6: The system of Example 5, in which the controller is configured to determine the correction factor and the maximum carbon dioxide concentration limit based on a model of a carbon dioxide concentration for the cabin.

Example 7: The system of Example 5, wherein the maximum carbon dioxide limit is a pre-determined carbon dioxide concentration limit.

Example 8: The system of any of Examples 1 to 7, in which the environmental control system includes at least one pressurized air source configured to generate pressurized air and at least one air conditioning pack configured to cool the pressurized air.

Example 9: The system of any of Examples 1 to 8, in which a tolerance of the concentration sensor at the first threshold concentration is less than the tolerance of the flow sensor at the flow rate setpoint.

Example 10. A system, including: a concentration sensor configured to measure a concentration of a contaminant in a cabin of an aircraft; a flow sensor configured to measure a flow rate of pressurized air to the cabin from an environmental control system; and a controller implemented in circuitry and in communication with the concentration sensor and the flow sensor, the controller configured to: control the flow rate of pressurized air into the cabin to maintain a concentration measurement of the contaminant in the cabin at or below a first concentration threshold; and control the flow rate of pressurized air into the cabin to maintain the flow rate of pressurized air into the cabin above a flow rate setpoint, in which the flow rate setpoint does not account for a tolerance of the flow sensor at the flow rate.

Example 11: The system of Example 10, in which the controller is configured to control the flow rate of pressurized air into the cabin based on the flow rate setpoint and a correction factor that is less than the tolerance of the flow sensor.

Example 12: A method, including: measuring, by a concentration sensor, a concentration of a contaminant in a cabin of an aircraft; measuring, by a flow sensor, a flow rate of air into the cabin; determining, by a controller, whether a concentration measurement of the contaminant in the cabin exceeds a first concentration threshold; at a first instance, in response to determining that the concentration measurement does not exceed the first concentration threshold, controlling, by the controller, the flow rate of pressurized air into the cabin based on a flow rate setpoint; and at a second instance, in response to determining that the concentration measurement exceeds the first concentration threshold, controlling, by the controller, the flow rate of pressurized air into the cabin based on the flow rate setpoint and a correction factor, wherein the correction factor is based on a tolerance of the flow sensor.

Example 13: The method of claim 12, further including: determining, by the controller, whether the concentration measurement exceeds a second concentration threshold; and at a third instance, in response to determining that the concentration measurement exceeds the first concentration threshold but does not exceed the second concentration threshold, controlling, by the controller, the flow rate of pressurized air into the cabin based on the flow rate setpoint and an increment of the correction factor.

Example 14: The method of Example 12 or 13, further including: receiving, by the controller, an indication of a number of occupants in the cabin; and determining, by the controller, the flow rate setpoint based on the number of occupants in the cabin and a minimum flow rate limit.

Example 15: The method of any of Examples 12 to 14, in which the contaminant comprises at least one of carbon dioxide or a hydrocarbon.

Example 16: The method of Example 15, in which the concentration sensor is a carbon dioxide sensor, and in which the first threshold is a maximum carbon dioxide limit associated with the flow rate setpoint.

Example 17: The method of Example 16, further including determining, by the controller, the correction factor and the maximum carbon dioxide concentration limit based on a model of a carbon dioxide concentration for the cabin.

Example 18: The method of Example 16, in which the maximum carbon dioxide limit is a pre-determined carbon dioxide limit.

Example 19: The method of any of Examples 12 to 18, further including: generating, by at least one pressurized air source of an environmental control system, the pressurized air; and cooling, by at least one air conditioning pack of the environmental control system, the pressurized air.

Example 20: The method of any of Examples 12 to 19, in which a tolerance of the concentration sensor at the first threshold concentration is less than the tolerance of the flow sensor at the flow rate setpoint.

Example 21: A method, including: measuring, by a concentration sensor, a concentration of a contaminant in a cabin of an aircraft; measuring, by a flow sensor, a flow rate of air into the cabin; controlling, by a controller the flow rate of pressurized air into the cabin to maintain a concentration measurement of the contaminant in the cabin at or below a first concentration threshold; and controlling, by the controller, the flow rate of pressurized air into the cabin to maintain the flow rate of pressurized air into the cabin above a flow rate setpoint, in which the flow rate setpoint does not account for a tolerance of the flow sensor at the flow rate.

Example 22: The method of Example 21, further including: controlling, by the controller, the flow rate of pressurized air into the cabin based on the flow rate setpoint and a correction factor that is less than the tolerance of the flow sensor Various examples have been described. These and other examples are within the scope of the following claims.

What is claimed is:

1. A system, comprising:
   an environmental control system configured to supply pressurized air to a cabin of an aircraft;
   a concentration sensor configured to output a signal indicative of a concentration measurement of a concentration of a contaminant in the cabin of the aircraft;
   a flow sensor configured to output a signal indicative of a flow rate measurement of a flow rate of the pressurized air into or out of the cabin, wherein the flow sensor is configured to provide the output indicative of the flow rate measurement within a flow sensor tolerance, and wherein the flow sensor tolerance is indicative of an accuracy of the flow rate sensor; and
   a controller implemented in circuitry and in communication with the concentration sensor and the flow sensor, the controller configured to:
      determine whether the concentration measurement exceeds a first concentration threshold, wherein the first concentration threshold is based on a flow rate setpoint;
      in response to determining that the concentration measurement does not exceed the first concentration threshold, control the flow rate of pressurized air into the cabin such that the flow rate measurement is at or above the flow rate setpoint; and
      in response to determining that the concentration measurement exceeds the first concentration threshold, control the flow rate of pressurized air into the cabin such that the flow rate measurement is at or above an incremented flow rate setpoint,
      wherein the incremented flow rate setpoint is based on the flow rate setpoint and a correction factor, and
      wherein the correction factor is based on the flow sensor tolerance.

2. The system of claim 1, wherein the controller is configured to:
   determine whether the concentration measurement exceeds a second concentration threshold; and
   in response to determining that the concentration measurement exceeds the first concentration threshold but does not exceed the second concentration threshold, control the flow rate of pressurized air into the cabin based on the flow rate setpoint and an increment of the correction factor.

3. The system of claim 1, wherein the controller is configured to:
   receive an indication of a number of occupants in the cabin; and
   determine the flow rate setpoint based on the number of occupants in the cabin and a minimum flow rate limit.

4. The system of claim 1, wherein the contaminant comprises at least one of carbon dioxide or a hydrocarbon.

5. The system of claim 4,
   wherein the concentration sensor is a carbon dioxide sensor, and
   wherein the first threshold is a maximum carbon dioxide concentration limit associated with the flow rate setpoint.

6. The system of claim 5, wherein the controller is configured to determine the correction factor and the maximum carbon dioxide concentration limit based on a model of a carbon dioxide concentration for the cabin.

7. The system of claim 1, wherein a tolerance of the concentration sensor at the first threshold concentration is less than the flow sensor tolerance at the flow rate setpoint, wherein the tolerance of the concentration sensor is indicative of an accuracy of the concentration measurement.

8. The system of claim 1, wherein the correction factor is a partial correction factor, wherein the partial correction factor is an increment of a full correction factor, wherein the full correction factor is based on the entire flow sensor tolerance.

9. The system of claim 1, wherein the incremented flow rate setpoint compensates for a portion of the flow sensor tolerance less than an entire flow sensor tolerance.

10. A system, comprising:
    a concentration sensor configured to output a signal indicative of a concentration measurement of a contaminant in a cabin of an aircraft;
    a flow sensor configured to output a signal indicative of a flow rate measurement of pressurized air to the cabin from an environmental control system wherein the flow sensor is configured to provide the output indicative of the flow rate measurement within a flow sensor tolerance, and wherein the flow sensor tolerance is indicative of an accuracy of the flow rate measurement; and
    a controller implemented in circuitry and in communication with the concentration sensor and the flow sensor, the controller configured to:
       control the flow rate of pressurized air into the cabin to maintain the concentration measurement in the cabin at or below a first concentration threshold, wherein the first concentration threshold is based on a flow rate setpoint by controlling the flow rate such that the flow rate measurement is at or above the flow rate setpoint, wherein the flow rate setpoint does not account for the flow sensor tolerance of the flow sensor at the flow rate.

11. The system of claim 10, wherein the controller is configured to control the flow rate of pressurized air into the cabin based on the flow rate setpoint and a correction factor that is less than the flow sensor tolerance.

12. A method, comprising:
    measuring, by a concentration sensor, a concentration measurement of a contaminant in a cabin of an aircraft, wherein the concentration sensor is configured to output a signal indicative of the concentration measurement;
    measuring, by a flow sensor, a flow rate measurement of a flow rate of pressurized air into or out of the cabin, wherein the flow sensor configured to output a signal indicative of the flow rate measurement, wherein the flow sensor is configured to provide the output indicative of the flow rate measurement within a flow sensor tolerance, and wherein the flow sensor tolerance is indicative of an accuracy of the flow rate sensor;

determining, by a controller, whether the concentration measurement exceeds a first concentration threshold, wherein the first concentration threshold is based on a flow rate setpoint;

at a first instance, in response to determining that the concentration measurement does not exceed the first concentration threshold, controlling, by the controller, the flow rate of pressurized air into the cabin such that the flow rate measurement is at or above the flow rate setpoint; and at a second instance, in response to determining that the concentration measurement exceeds the first concentration threshold, controlling, by the controller, the flow rate of pressurized air into the cabin such that the flow rate measurement is at or above an incremented flow rate setpoint, wherein the incremented flow rate setpoint is based on the flow rate setpoint and a correction factor, wherein the correction factor is based on the flow sensor tolerance.

13. The method of claim 12, further comprising:

determining, by the controller, whether the concentration measurement exceeds a second concentration threshold; and at a third instance, in response to determining that the concentration measurement exceeds the first concentration threshold but does not exceed the second concentration threshold, controlling, by the controller, the flow rate of pressurized air into the cabin based on the flow rate setpoint and an increment of the correction factor.

14. The method of claim 12, further comprising:

receiving, by the controller, an indication of a number of occupants in the cabin; and determining, by the controller, the flow rate setpoint based on the number of occupants in the cabin and a minimum flow rate limit.

15. The method of claim 12, wherein the contaminant comprises at least one of carbon dioxide or a hydrocarbon.

16. The method of claim 15, wherein the concentration sensor is a carbon dioxide sensor, and wherein the first threshold is a maximum carbon dioxide limit associated with the flow rate setpoint.

17. The method of claim 16, further comprising determining, by the controller, the correction factor and the maximum carbon dioxide concentration limit based on a model of a carbon dioxide concentration for the cabin.

18. The method of claim 16, wherein the maximum carbon dioxide limit is a pre-determined carbon dioxide limit.

19. The method of claim 12, further comprising:

generating, by at least one pressurized air source of an environmental control system, the pressurized air; and cooling, by at least one air conditioning pack of the environmental control system, the pressurized air.

20. The method of claim 12, wherein a tolerance of the concentration sensor at the first threshold concentration is less than the tolerance of the flow sensor at the flow rate setpoint.

* * * * *